(12) United States Patent
Hirota et al.

(10) Patent No.: US 7,074,986 B1
(45) Date of Patent: Jul. 11, 2006

(54) CONSTRUCTION OF BARLEY WITH REDUCED GEL PROTEIN CONTENT

(75) Inventors: Naohiko Hirota, Nitta-machi (JP); Makoto Kihara, Nitta-machi (JP); Kazutoshi Ito, Nitta-machi (JP)

(73) Assignee: Sapporo Breweries Limited, Tokyo (JP)

( * ) Notice: Subject to any disclaimer, the term of this patent is extended or adjusted under 35 U.S.C. 154(b) by 603 days.

(21) Appl. No.: 10/048,987

(22) PCT Filed: Aug. 16, 2000

(86) PCT No.: PCT/JP00/05476

§ 371 (c)(1),
(2), (4) Date: Feb. 19, 2002

(87) PCT Pub. No.: WO01/11946

PCT Pub. Date: Feb. 22, 2001

(30) Foreign Application Priority Data

Aug. 16, 1999 (JP) ............................. P11-229696

(51) Int. Cl.
*A01H 5/00* (2006.01)
*C12N 15/82* (2006.01)

(52) U.S. Cl. .................. 800/286; 536/23.1; 435/320.1; 800/320

(58) Field of Classification Search ................ 800/295; 536/23.1; 435/320
See application file for complete search history.

(56) References Cited

FOREIGN PATENT DOCUMENTS

WO       98/03655       1/1998

OTHER PUBLICATIONS

Doerks et al. Protein annotation: detective work for function prediction. Trends Genet. Jun. 1998 vol. 14(6):248-250.*
Shen et al. Eur J. Biochem. 2001. vol. 268, pp. 2331-2337.*
Sorensen et al. Mol Gen Genet. 1996. vol. 250(6), pp. 750-760.*
Brennan et al. J. Cereal Science. 1998. vol. 28, pp. 291-299.*
Onate et al. J Biol Chem. 1999. vol. 274(14), pp. 9176-9182.*

Journal of Cereal Science, vol. 28 [3], pp. 291-299 1998.
Molecular and General Generics, vol. 217, pp. 195-201 1989.
Molecular and General Generics, vol. 250, pp. 750-760 1996.
D82941 Accession No., NCBI, National Library of Medicine USA, Bethesda, MD, 1996.
P.R. Shewry: "Barley Seed Proteins" Barley: Chemistry and Technology, pp. 131-197.
E.D. Baxter: "Sulfur-Containing Hordeins and Their Importance in Malting and Brewing" Brewer's Digest, pp. 45-47 Nov. 1980.
R. Van Den Berg et al.: "Proteins from Barley to Wort" EBC Congress, pp. 461-469 1981.
Derek B. Smith et al.: "Gel-Forming Proteins in Barley Grain and their Relationships with Malting Quality" Journal of Cereal Science, pp. 229-239 Jun. 3, 1983.
Derek B. Smith et al.: "Relationships of Barley Proteins Soluble in Sodium Dodecyl Sulphate to Malting Quality and Varietal Identification" Journal of Cereal Science, pp. 185-197 Feb. 21, 1983.
J.H. Skerritt et al.: "Disulphide-bonded 'Gel Protein' Aggregates in Barley: Quality-related Differences in Composition and Reductive Dissociation" Journal of Cereal Science, pp. 219-235 Apr. 27, 1992.
K.A. Howard et al.: "The Relationship Between D Hordein and Malting Quality in Barley" Journal of Cereal Science, pp. 47-53 Mar. 23, 1995.

(Continued)

*Primary Examiner*—David H Kruse
(74) *Attorney, Agent, or Firm*—Oblon, Spivak, McClelland, Maier & Neustadt, P.C.

(57) ABSTRACT

In barley, the formation of D-hordein constituting gel protein is to be reduced. This reduction in the formation of D-hordein causes a reduction of gel protein because D-hordein fraction decreases in the gel protein; and in addition, it brings about the transformation (reduction) of proteins other than D-hordein which constitute the gel protein from the gel protein. Therefore, by introducing into barley D-hordein expression suppressing vector 1 capable of suppressing the D-hordein formation and transforming the barley therewith, it is possible to attain the reduction of gel protein based on the reduction in the D-hordein formation.

12 Claims, 6 Drawing Sheets

OTHER PUBLICATIONS

H. Funatsuki et al.: "Fertile transgenic barley generated by direct DNA transfer to protoplasts" Theor. Appl. Genet., pp. 707-712 Jan. 17, 1995.

M.G. Murray et al.: "Rapid isolation of high molecular weight plant DNA" Nucleic Acids Research, vol. 8, No. 19, pp. 4321-4325 Aug. 25, 1980.

K.A. Howard et al.: "The relationship between D hordein and malting quality in barley" Journal of Cereal Science, vol. 24, No. 1, pp. 47-53 1996.

K. Gayler: "Investigation of genes affecting barley malting quality" Online!, XP002229716, Oct. 25, 1995 Retrieved from the Internet: <URL:http://128,250.58.34/staff/kg.htm>, Feb. 14, 2003.

* cited by examiner

PROVIDED SAMPLES

Fig.5B

PROVIDED SAMPLES

Fig.6

SEQUENCE LISTING

<160> NUMBER OF SEQ ID NOS: 4

<210> SEQ ID NO 1
<211> LENGTH: 2434
<212> TYPE: DNA
<213> ORGANISM: Barley

<400> SEQUENCE: 1

```
caaaactaga gatcaattca ttgacagtcc accgagatgg ctaagcggct ggtcctcttt      60
gtggcggtaa tcgtcgccct cgtggctctc accaccgctg aacgtgagat caatgggaac     120
aacattttcc ttgatagccg ctctaggcag ctacagtgtg agcgcgagct ccaggagagc     180
tcgctcgagg cgtgccggcg ggtcgtggac caacagctgg ttggccagct gccatggagc     240
acggggctcc agatgcagtg ctgccagcag cttcgggacg tcagccccga gtgccgcccc     300
gtcgccctca gccaggtcgt gaggcaatac gagcagcaaa ccgaggtgcc atccaaggga     360
ggatccttct acccgggcgg gaccgcaccg ccgctgcagc aaggaggatg gtggggaacc     420
tctgtaaaat ggtactaccc agaccaaact tcttcgcaac agtcatggca agggcaacaa     480
gggtaccacc aaagcgtaac ttcttcccag cagccaggac aagggcagca aggtcctac      540 ccaggttcaa ctttcccgca gcagccagga caaggacaac aaccaggaca gaggcagcca     600
```

-continued

```
tggtcctatc caagtgcaac tttcccacaa cagccagggc aagggcaagg gcaacaaggg      660
tactacccag gcgcaacttc cctgctgcag ccaggacaag ggcaacaagg gccctaccag      720
agtgcaactt ctccacagca gccaggacaa ggacagggac aacaagagac ctatccaatt     780
gcaacttccc cgcatcagcc aggacaatgg caacaaccag gacaagggca acaagggtac     840
tacccaagtg taacttctcc acaacagtcg ggacaagggc aacaaggta cccaagtaca      900 acttctccac aacaatcggg gcaagggcaa cagctgggac aagggcaaca accaggacaa     960
gggcaacaag ggtacccaag tgcaactttt ccacaacagc caggacaatg gcaacaaggg    1020
tcctacccaa gtacaacttc tccgcagcag tcaggacaag gcaacaagg gtacaaccca     1080 agtggaactt ctacgcagca gccgggacaa gtgcaacagt tgggacaagg gcaacaaggg    1140
tactacccaa ttgcaacttc tccgcagcag ccaggacaag ggcaacagct aggacaaggg    1200
caacaaccag gacatgggca acagctagtg caagggcaac aacaaggaca agggcaacaa    1260
ggacactacc caagtatgac ttctccgcac caaacaggac aagggcaaaa aggatactac    1320
ccaagtgcaa tttctccgca gcagtcagga caaggacaac aaggatacca gcctagtgga    1380
gcttcttcac agggggtcggt gcaagggggcg tgccagcaca gcacatcttc tccgcagcag    1440
caagcacaag ggtgccaagc ttcttcacca aagcaagggc tagggtcgtt gtactacccg    1500
agtggagctt atacacaaca gaaaccaggg caagggtaca cccaggtgg aacttctccg     1560 ctgcaccagc aagggggagg gttcggcggc gggttaacga cggagcaacc gcagggagga    1620
aagcagccat tccattgcca gcaaaccact gtctcccctc accagggtca gcaaaccact    1680 gtttccccctc atcagggtca gcaaaccact gtctcccctc atcagggtca gcaaaccact    1740
gtctcccctc accagggtca gcaaaccacc gtctcccctc accagggtca gcaaaccacc    1800
gtctcccctc atcagggtca gcaaaccact gtctcccctc atccgggtca gcaaaccact    1860
gtctcccctc atcagggtca gcaaaccact gtctcccctc atccgggtca gcaaaccact    1920
gtctcccctc atcagggtca gcaaaccact gtctcccctc atcagggtca gcaaaccacc    1980
gtctcccctc atcagggtca gcaaaccacc gtctcccctc atcagggtca gcaaaccacc    2040
gtctcccctc atcagggtca gcagcccggc gagcagcctt gcggtttccc tggccagcaa    2100
accaccgtgt ctctgcacca tggtcagcag tccaacgagt tgtactacgg cagcccctac    2160
catgttagcg tggagcagcc gtcggccagc ctaaaggtag caaaggcgca gcagctcgcg    2220
gcgcagctgc cggcaatgtg tcggctggag ggcggcggcg gcctgttggc cagccagtag    2280
tagaactctg gcagctcgca tggtgcttgg gcatgcatgc accttagcta tacaataaac    2340
gtgacgtgtg cttgcagttt ttcatgtaac tagggtaaaa cccaacaata atgcaaaacg    2400
gaaagcttct ccatccaaaa aaaaaaaaaa aaaa                                2434
```

<210> SEQ ID NO 2
<211> LENGTH: 2380
<212> TYPE: DNA
<213> ORGANISM: Barley

<400> SEQUENCE: 2

```
gaattcattg acagtccacc gagatggcta agcggctggt cctctttgtg gcggtaatcg     60
tcgccctcgt ggctctcacc accgctgaac gtgagatcaa tgggaacaac attttccttg    120
atagccgctc taggcagcta cagtgtgagc gcgagctcca ggagagctcg ctcgaggcgt    180
gccggcgggt cgtggaccaa cagctggttg gccagctgcc atggagcacg gggctccaga    240
```

| | |
|---|---|
| tgcagtgctg ccagcagctt cgggacgtca gccccgagtg ccgccccgtc gccctcagcc | 300 |
| aggtcgtgag gcaatacgag cagcaaaccg aggtgccatc caagggagga tccttctacc | 360 |
| cgggcgggac cgcaccgccg ctgcagcaag aggatggtg gggaacctct gtaaaatggt | 420 |
| actacccaga ccaaacttct tcgcaacagt catggcaagg caacaaggg taccaccaaa | 480 |
| gcgtaacttc ttcccagcag ccaggacaag ggcagcaagg gtcctaccca ggttcaactt | 540 |
| tcccgcagca gccaggacaa ggacaacaac caggacagag cagccatgg tcctatccaa | 600 |
| gtgcaacttt cccacaacag ccagggcaag gcaagggca acagggtac acccaggcg | 660 |
| caacttccct gctgcagcca ggacaagggc aacaagggcc taccagagt gcaacttctc | 720 |
| cacagcagcc aggacaagga cagggacaac aagagaccta tccaattgca acttccccgc | 780 |
| atcagccagg acaatggcaa caaccaggac aagggcaaca agggtactac ccaagtgtaa | 840 |
| cttctccaca acagtcggga caagggcaac aagggtaccc aagtacaact tctccacaac | 900 |
| aatcggggca agggcaacag ctgggacaag gcaacaacc aggacaaggg caacaagggt | 960 |
| acccaagtgc aacttttcca acagccag gacaatggca acaagggtcc tacccaagta | 1020 |
| caacttctcc gcagcagtca ggacaagggc aacaagggta cacccaagt ggaacttcta | 1080 |
| cgcagcagcc gggacaagtg caacagttgg gacaagggca acagggtac acccaattg | 1140 |
| caacttctcc gcagcagcca ggacaagggc aacagctagg acaagggcaa caaccaggac | 1200 |
| atgggcaaca gctagtgcaa gggcaacaac aaggacaagg gcaacaagga cactacccaa | 1260 |
| gtatgacttc tccgccaccaa acaggacaag ggcaaaaagg atactaccca agtgcaattt | 1320 |
| ctccgcagca gtcaggacaa ggacaacaag gataccagcc tagtggagct tcttcacagg | 1380 |
| ggtcggtgca aggggcgtgc cagcacagca catcttctcc gcagcagcaa gcacaagggt | 1440 |
| gccaagcttc ttcaccaaag caagggctag ggtcgttgta ctacccgagt ggagcttata | 1500 |
| cacaacagaa accagggcaa gggcacaacc caggcggaac ttctccgctg caccagcaag | 1560 |
| ggggagggtt cggcggcggg ttaacgacgg agcaaccgca gggaggaaag cagccattcc | 1620 |
| attgccagca aaccactgtc tcccctcacc agggtcagca aaccactgtt tccctcatc | 1680 |
| agggtcagca aaccactgtc tccctcatc agggtcagca aaccactgtc tccctcacc | 1740 |
| agggtcagca aaccaccgtc tcccctcacc agggtcagca aaccaccgtc tccctcatc | 1800 |
| agggtcagca aaccactgtc tccctcatc cgggtcagca aaccactgtc tccctcatc | 1860 |
| agggtcagca aaccactgtc tccctcatc cgggtcagca aaccactgtc tccctcatc | 1920 |
| agggtcagca aaccactgtc tccctcatc agggtcagca aaccaccgtc tccctcatc | 1980 |
| agggtcagca aaccaccgtc tccctcatc agggtcagca aaccaccgtc tccctcatc | 2040 |
| agggtcagca gcccggcgag cagccttgcg gtttccctgg ccagcaaacc accgtgtctc | 2100 |
| tgcaccatgg tcagcagtcc aacgagttgt actacggcag cccataccat gttagcgtgg | 2160 |
| agcagccgtc ggccagccta aagtagcaa aggcgcagca gctcgcggcg cagctgccgg | 2220 |
| caatgtgtcg gctggagggc ggcggcggcc tgttggccag ccagtagtag aactctggca | 2280 |
| gctcgcatgt tgcttgggca tgcatgcacc ttagctatac aataaacgtg acgtgtgctt | 2340 |
| gcagttttc atgtaactag ggtaaaaccc aacaataatg | 2380 |

<210> SEQ ID NO 3
<211> LENGTH: 1739
<212> TYPE: DNA
<213> ORGANISM: Barley

<400> SEQUENCE: 3

-continued

```
ctgcagattt gcaaaagcaa tgactaacag atacatatat tgcaaaaaaa acagaggata      60
atcactttta ttagatgaaa taaacagatc aatttacata agtcctcact tctccaaaca     120
gtattcagga ccatgataaa accgattacg tagctctgtt ttggaagatc caaatcctca     180
agttgagttt cattaattgg aatcgattgt atgctaaaca cgatgaacaa atggtgggtt     240
acgtggcata gcatacaact attcccctat tattctgcat gcatgatctc aatcggactc     300
cttcctagtt cctagttggc tctgctttga actttcatcc acatctcttt gagttattat     360
taacagacgc aagaaacatt tttttgcgct aagccaaggt gaggcaaggt cgcattggag     420
gactgatgga ctggcttcga tggattatga tatactcggt tttgcctgtt tgactgttac     480 gttttttctaa ttttgtggtt aggaattttt cgccgcagag tatagaataa ctaagctcaa    540
cacaaacaat ttagcaagca cattaaactg ggatcgtagg agcgcacctg gattttgttg     600
gttgatggtg gatgaaatgg gtgaatttaa taactgatat agtgtcagtg caacggaagc     660
ccatttttca tacaagttat taatattgtc aacatttgtc aacaaacaaa tgtttaactc     720
aggtttgcaa ttatgaagcc ccaattataa gaaggggata ttatgatggc gtgagcaagt     780
gataaggcca aggggagaag aagtgcagca tctacgcagc ccagtgaaag atagtgaaaa     840
tacagagagg cagggacggg ggagcaacac atggaaatca tagaagaaca aaagagttta     900
aacataggag gcagatataa tggacagcta aatctgcatt atctcatttg ggaaatgaaa     960
aaaataatcc tattcttgtg taaatcaaaa ctatttgccg cgaattttct tcgaagatcc    1020
tgtgttaatt ttagacacgg ctgaccaaag gttttcaatt agttgagttt tgtcacggaa    1080
aggtgtttcc atacatccaa aaattctaaa aacttttga tacggcgcgt tcgtagcata     1140
gctagatgtt gtgagtcact ggatagatat tgtgagtcat atcgtggatt tgtgttgcct    1200
gcaaatccaa ctacatgaca agcaacaaat gagcttttgg aaagatgatt tctcaattta    1260
ccagttccat gcaagctacc ttccactact cgacatgctt aaaagcttcg agtgcccgcc    1320
gatttgccag caatggctaa cagacacata ttctgccaaa accccagaac aataatcact    1380
tctcgtagat gaagagaaca gaccaagata caaacgtcca cgcttcagca aacagtaccc    1440
cagaactagg attaagccga ttacgcggct ttagcagacc gtccaaaaaa actgttttgc    1500
aaagctccaa ttcctccttg cttatccaat ttcttttgtg ttggcaaact gcacttgtcc    1560
aaccgatttt gttcttcccg tgtttcttct taggctaact aacacagccg tgcacatagc    1620
catggtccgg aatcttcacc tcgtccctat aaaagcccag ccaatctcca caatctcatc    1680
atcaccgaga acaccgagaa ccacaaaact agagatcaat tcattgacag tccaccgag    1739
```

<210> SEQ ID NO 4
<211> LENGTH: 1274
<212> TYPE: DNA
<213> ORGANISM: Barley

<400> SEQUENCE: 4

```
atcgaagcct ccatgctcac tctttcgtcg gcttctcttt atcatccacc tccttcttca      60
cctttcccaa cttgaccgtc aagcacttca agatcctaac acggacagtt tctacgatta     120
tttttgcatc gtcatccaac acattcatgt tcaaggtcaa catctttata tcttccgaaa     180
cggtcgcgag ctcaacttgc tcatagtttt tttaggcagc agaagttggc ccgaaacttt     240
aaaccaaaca cagcgtaaat ttaccatcat tacaccaata attgccataa aaaatattcc     300
tatttgattt actatgctta ttattaaaaa tccgacatta tatttttttt tctgttcatg     360
```

-continued

```
agtcacaact attcccttttt tttcagacgg aaatcgcagt tattgccgac atactactaa      420
tgtcgatgta cacggtccac atttaccgcc caagtttaat gtgaccgcac ctaaagaaaa      480
gaaaaagtta atgtcaccgc acacagacgg acccacctaa cagctggccc acgctgcctt      540
ctatgcgcct tccacgaaga aatccggccc cacctgccgg tgaccctcca agcacgtccc      600
tatatagact tcctcgtgtg cggccatctc ggtctctctc tctctcctcc attcctctct      660
cctcctcctg ccaccgatcc caaaccaggg aggaacccgg cgcgaggagg gcaaaggaag      720
agaagaggag accacccagc cgaccgcgcg accgcacgca cagggcagca gccgtcgcga      780
tcccggtaac caccattcgc cggatctctc cttcccccgt cgcccctcct gtgatccgat      840
cggtggtttg gtcgctcgat tcgtccctat attttcgtt gttgtaccg gcttcacctg        900 tttagtggtt cgggtgtgtt cgatctcatc atcctgtcgg tgtccggtag attcgatccg      960
tttctcgagg gtgcggctcg aggaatctgc cgcgtttgac cggcttcggt cggcccagcg     1020
ttgttctcac gcggggtgct cgggaatccc gcgcggagcc ggtcgcgaat ctggtccggt     1080
ttagcgctgt tcgtgcgccg tggcgtggat ctggcgctgc tgccctcaga tcttgtagat     1140
ctagttgggt ggcttcaatt ctggagtatt tttttattgt tgttattata gaacgagcct     1200
gtgtctgtgt tgatctatgg gtctgacgct tcggccttga atttgtttcg tttgatttca     1260
gcgcaggagc ggac                                                       1274
```

CONSTRUCTION OF BARLEY WITH REDUCED GEL PROTEIN CONTENT

TECHNICAL FIELD

This invention relates to the construction of barleys in which gel protein is reduced in barley seeds.

BACKGROUND ART

In the seed of barley (*Hordeum vulgare*), proteins specifically expressed therein (seed storage proteins) are present in large quantities, 35–55% of which are comprised of alcohol-soluble hordeins (Shewry 1993, Barley: Chemistry and Technology. pp. 164: American Association of Cereal Chemists).

These hordeins are classified into four types, B, C, D, and γ based on their loci, amino acid compositions, etc; and the content ratio of each to the total hordein is from 70 to 80% for B, from 10 to 20% for C, and 5% or less for D.

It has been reported that these hordeins have a critical role in brewery as amino acid sources for yeast as well as have influence on the color of beer and on the haze formation upon its cooling. These reports did not examine individually classified hordeins, but examined the whole hordeins for their influence on beer quality and beer manufacturing process.

Specifically, Baxter discovered that addition of a reducing agent to mash improved the filtration speed of wort (Baxter, 1980, Brewers Digest 55: 45–47). Furthermore, van den Berg et al. reported that gel protein aggregates, i.e., gel proteins, which are pelleted by centrifugation after the protein extraction with 1.5% SDS from barley exert a detrimental influence on the filterability of wort (van den Berg et al. 1981, Proceeding of the EBC Congress, Copenhagen, 47: 461–469). These reports suggest the correlation between the gel protein resulting from the polymerization of B- and D-hordeins via. disulfide bonds and the wort filterability.

In addition, it has been reported that this gel protein has a highly negative correlation with malt extract (Smith and Lister (1983), Journal of Cereal Science 1: 229–239; Smith and Simpson (1983), Journal of Cereal Science 1: 185–197; Skerritt and Janes (1992), Journal of Cereal Science 16: 219–235; and Howard et al. (1996), Journal of Cereal Science 24: 47–53).

Furthermore, Brennan et al. examined the presence and absence of D-hordein as well as the gel protein content by utilizing isogenic lines based on the barley line which lacked D-hordein, and suggested correlation between the two (Brennan et al. (1998), Journal of Cereal Science 28: 291–299).

From such a standpoint, it has been suggested that if the gel protein can be reduced by some means, there will be the possibility of improving the wort filterability and the wort extract yield.

DISCLOSURE OF THE INVENTION

As for the method for reducing gel protein, a method by which a barley line having a low gel protein content is used as one parent for crossing (Brennan et al. (1998), Journal of Cereal Science 28: 291–299) or a method relying on mutation breeding by radiation exposure or the like has been employed thus far; however, either of these methods cannot be said to be an efficient method.

Specifically, the method utilizing crossing described above will require considerable time, labor, breeding fields and adequate breeding technologies in order to produce the objective varieties or lines in which gel protein has been reduced. In addition, it will be necessary that a great number of lines be provided and tested for selection. Therefore, this method has rendered it extremely difficult to attempt the construction of barley with reduced gel protein content in an economical and efficient manner.

Further, in the other method, which is a method for inducing mutants by utilizing radiation or the like, the occurrence of mutation is low and in addition, the positions at which mutation is inserted are random; this requires mutagenesis testing on a considerable scale in order to produce the objective mutants. Furthermore, special facilities are needed to carry out such radiation exposure, which results in the problem that the places suitable for the manipulations of construction are limited.

On the other hand, as molecular biology has advanced in recent years, methods for altering plants through genetic engineering have been developed; the gene transformation technologies of barley have been developed and improved, including PEG-protoplast technique, particle bombardment, and the *Agrobacterium* technique. This has allowed transformed barley to be produced with relative ease and within a short period of time.

Accordingly, the present inventors have eagerly repeated research to solve these various problems and as a result, have utilized the gene transformation technology to develop a method for constructing a barley with reduced gel protein content in an economical and efficient manner.

This invention aims at reducing the gel protein content in barley by suppressing the production of the D-type (i.e., D-hordein) contained in the hordeins in a minute amount. This invention has resulted from the finding by the present inventors that by suppressing the D-hordein production, it will be possible to reduce the gel protein content more than expected, although D-hordein occupies only about 5% of the total hordein.

Specifically, this invention relates to a method for constructing a barley with reduced gel protein content in which the gel protein capable of agglutinating in a gel during the extraction of proteins from the barley has been reduced, said method comprising introducing into the barley, a D-hordein expression suppressing nucleic acid capable of suppressing the production of the endogenous D-hordein protein of barley, whereby the production of D-hordein is suppressed by introduction of the D-hordein expression suppressing nucleic acid and the gel protein content is thus reduced.

According to the above-mentioned invention, a D-hordein expression suppressing nucleic acid is introduced into a barley to cause the production of the D-hordein protein to be suppressed, which allows for a reduction in the D-hordein protein fraction within the gel protein. This D-hordein protein comprises only a very small portion of the gel protein. Despite that, the reduction of this D-hordein protein, which constitutes only the very small portion, also makes it possible to eliminate or reduce from the gel protein, other proteins that constitute said gel protein. Consequently, this invention allows the total gel protein content to be reduced more than expected.

In the above-mentioned invention, this particular invention is characterized in that the D-hordein expression suppressing nucleic acid can express an antisense RNA complementary to the endogenous D-hordein RNA of barley.

According to the above-mentioned invention, the antisense D-hordein RNA is expressed in the barley and is hybridized to the endogenous D-hordein RNA; its translation into a protein is inhibited and thus, it will become possible to suppress the production of the D-hordein protein.

This invention relates to a D-hordein expression suppressing nucleic acid for generating an antisense RNA that can be complementary to the endogenous D-hordein RNA produced in barley, which is characterized in that a D-hordein coding sequence encoding D-hordein is linked to the downstream of a promoter operable within the barley in a reverse orientation so as to be able to generate the antisense RNA.

The D-hordein expression suppressing nucleic acid according to this invention transcribes the antisense D-hordein RNA from the promoter; and this antisense D-hordein RNA binds to the endogenous D-hordein RNA in a complementary manner and inhibits translation of the D-hordein protein from the D-hordein RNA.

The D-hordein expression suppressing nucleic acid according to this invention is characterized in that the D-hordein coding sequence comprises any one of: (1) the nucleotide sequence set forth in SEQ ID NO:1; (2) the nucleotide sequence set forth in SEQ ID NO:2; (3) the nucleotide sequence set forth in SEQ ID NO:1 having at least one of substitution, deletion, addition, and insertion, said nucleotide sequence encoding a RNA that can be complementary to the endogenous D-hordein RNA of barley; and (4) the nucleotide sequence set forth in SEQ ID NO:2 having at least one of substitution, deletion, addition, and insertion, said nucleotide sequence encoding a RNA that can be complementary to the endogenous D-hordein RNA of barley.

These nucleotide sequences can suppress the production of D-hordein protein by their expression and the consequent binding to the endogenous D-hordein RNA in a complementary manner.

This invention also relates to a vector comprising the D-hordein expression suppressing nucleic acid.

Thus, by linking the expression suppressing nucleic acid to the vector, it will become possible to stably retain an expression cassette as well as to cause the expression cassette to be generated through amplification as required.

This invention is characterized in that a selection marker expression cassette capable of expressing a selectable marker is provided in the vicinity of the D-hordein expression suppressing nucleic acid.

According to the above-mentioned invention, by providing the selection expression cassette, it will be possible to select the line into which the D-hordein expression suppressing nucleic acid has been introduced with the aid of the selection marker and to quickly identify the line in which the expression of D-hordein is suppressed, i.e., the line with reduced gel protein.

A kit for constructing a barley with reduced gel protein content according to this invention comprises the D-hordein expression suppressing nucleic acid or the vector described above and is characterized in that it introduces the D-hordein expression suppressing nucleic acid or the vector into the barley so as to reduce the gel protein content of barley.

According to this invention, the inclusion of the D-hordein expression suppressing nucleic acid or the vector allows the barley with reduced gel protein content to be produced conveniently by simply introducing it into the barley and by subjecting it to transformation.

This invention also encompasses the barley produced by any of the methods for constructing a barley with reduced gel protein content as described above or by the kit for constructing a barley with reduced gel protein content as described in any of claims 8–9.

By utilizing the barley of this invention, improvements on the wort filterability and the wort extract yield which are presumably correlated with the gel protein content can be expected, since only the content of D-hordein, which is regarded as minute in quantity among hordeins, is reduced with the aim towards reducing the gel protein.

BEST MODE FOR CARRYING OUT THE INVENTION

Preferred embodiments of this invention will be described hereafter.

1. Method for Suppressing the Expression of D-hordein Gene

Since D-hordein protein undergoes the process of transcription of a chromosomal gene to RNA and translation of the RNA into the protein, suppression of the expression of D-hordein in barley can be carried out by suppressing either of these stages.

As for the method for suppressing the expression of the D-hordein protein, the antisense method, co-suppression method, the ribozyme method and the like are mentioned, for example. In addition to the method for inhibiting the production stage of the D-hordein protein, its expression may be suppressed by modifying the D-hordein gene domain on which the production of this D-hordein protein is based. Such expression-suppressing method, for example, may employ gene targeting.

For the purpose of suppressing the expression of D-hordein, any of the above-mentioned methods may be employed insofar as it is capable of suppressing the expression of D-hordein in the manner thus described; however, the antisense method can preferably be utilized as a method with high reliability and specificity.

2. Construction of Nucleic Acids for Suppressing the Expression of D-hordein Gene The construction of a nucleic acid for suppressing the expression of D-hordein differs depending on the expression-suppressing method to be employed.

(1) Antisense Method

The antisense method inhibits the translation of an objective D-hordein mRNA into protein by causing an antisense RNA to specifically bind to the D-hordein mRNA. Therefore, when the antisense method is employed, the antisense D-hordein RNA can be used as an expression suppressing nucleic acid, and the expression of the D-hordein protein can be suppressed by supplying barley with this antisense RNA directly.

In addition, for this expression suppressing nucleic acid, an expression cassette capable of expressing the antisense RNA can preferably be employed. By using this expression cassette to transform barley, it is possible to stably provide a transformed barley with the antisense RNA and to allow the next generation seed group derived from this transformant to inherit this trait.

The above-mentioned antisense D-hordein expression cassette can be constructed in the following manner. The barley D-hordein gene is operably linked to the downstream of a promoter to be expressed in the endosperm tissue of ripening barley in a reverse orientation and a transcription termination factor that similarly functions in the endosperm tissue of ripening barley is further linked to its downstream, which can accomplish the construction.

Here, the "barley D-hordein gene" is linked to the downstream of the promoter in a reverse orientation so that the antisense RNA can be generated. It is not necessary for this "barley D-hordein gene," which has been introduced into an expression cassette, to have the whole region of the D-hordein gene; and the gene may be a partial sequence of the D-hordein gene insofar as it is provided with the length sufficient to be able to inhibit the translation of the endogenous D-hordein mRNA.

Conversely, the "barley D-hordein gene" in the cassette may be longer than the endogenous D-hordein mRNA, or may be that which an arbitrary DNA fragment is attached to, insofar as it is capable of inhibiting the translation of the endogenous D-hordein mRNA in the same manner as above.

For the barley D-hordein gene, the sequence set forth in SEQ ID NO:1 or in SEQ ID NO:2 can preferably be used, for example, and sequences substantially identical to those sequences can also be used. These substantially identical sequences have at least one of substitution, deletion, addition, and insertion within the above-mentioned sequence; and they are the sequences capable of suppressing the expression of the endogenous D-hordein gene.

The transgene in the expression cassette is not limited to the "barley D-hordein gene", and genes highly homologous to the D-hordein gene can be used. For example, even high molecular weight wheat glutenin subunit genes or high molecular weight rye secalin genes can be used insofar as they are capable of binding to the endogenous D-hordein mRNA in a complementary manner.

The transgene in the expression cassette to be used here may be a genomic DNA, cDNA, or a gene manipulated from the foregoing gene by synthesis or alternation.

The "promoter" in the expression cassette is not particularly limited insofar as it possesses promoter activity in the endosperm tissue of ripening barley. For example, there are mentioned a B-hordein promoter, a C-hordein promoter, a γ-hordein promoter, a β-amylase promoter, a high molecular weight glutenin subunit promoter, a high molecular weight rye secalin promoter, a CaMV35S promoter, and an actin promoter.

In addition, there is no limitation to the transcription termination factor insofar as it functions in the endosperm tissue of ripening barley; for example, a NOS terminator and the like may be used.

(2) Co-Suppression Method

According to the co-suppression method, the D-hordein gene is, for example, linked as a transgene to the downstream of the promoter to be expressed in the endosperm tissue of ripening barley in a normal orientation, and a transcription termination factor such as the NOS terminator is linked to the further downstream thereof, which accomplish the construction of a D-hordein expression suppressing nucleic acid.

The transgene to be used here is a DNA fragment requisite for D-hordein reduction; and, for example, a D-hordein gene can preferably be employed. This transgene can also be inserted between the promoter and the transcription termination factor in a normal orientation. In addition, it is not necessary for the transgene to contain the whole region that is expressed as mRNA, and even a short gene segment may be adequate. Conversely, the transgene may be longer than the whole region that is expressed as mRNA and even a segment to which an arbitrary DNA fragment is attached may be adequate.

Any genes other than the D-hordein gene can be used as the transgene insofar as they are highly homologous to the D-hordein gene. Specifically, high molecular weight wheat glutenin subunit genes or high molecular weight rye secalin subunit genes may be used.

The transgene to be used here may be a genomic DNA, cDNA, or a gene manipulated from the foregoing gene by synthesis or alternation.

Anything may be suitable for the "promoter" insofar as it has promoter activity in the endosperm tissue of ripening barley. Specifically, there are mentioned a B-hordein promoter, a C-hordein promoter, a γ-hordein promoter, a β-amylase promoter, a high molecular weight glutenin subunit promoter, a high molecular weight rye secalin promoter, a CaMV35S promoter, and an actin promoter.

(3) Ribozyme Method

The ribozyme method is a method by which ribozyme (RNA enzyme) decomposes D-hordein mRNA to suppresses the expression of D-hordein. Therefore, the D-hordein gene expression suppressing nucleic acid for use in this method can be constructed by preparing the gene that codes the ribozyme designed so as to be able to decompose the D-hordein mRNA being expressed and linking said gene between the promoter and the transcription termination factor in a normal orientation as described above.

(4)

The construction of the D-hordein expression suppressing nucleic acid as described above requires manipulations related to gene cloning such as restriction enzyme treatment, DNA ligation, and transformation of E. coli., and these may be performed using conventional techniques. For example, Molecular Cloning (Sambrook, Fritsch, Maniatis, Cold Spring Harbor Laboratory) may be referred to.

The cassette for suppressing the expression of specific genes as described in this section can be introduced into the chromosome of a plant intact in a linearized form, or alternatively it can be incorporated into an arbitrary plasmid and can be used as an expression vector for suppressing the expression of specific genes, which will be described.

3. Construction of Vector for Suppressing the Expression of Specific Gene

The expression suppressing nucleic acid described above can directly be used as a nucleic acid fragment, or alternatively it can be used as an expression-suppressing vector by being inserted into a vector. The expression-suppressing vector can be constructed by inserting the expression suppressing nucleic acid into an arbitrary plasmid. The expression-suppressing vector can be constructed concurrently with the expression suppressing nucleic acid by sequentially linking a promoter, a structural gene, and a transcription termination factor to the arbitrary plasmid.

For the plasmid that can be used here, although any plasmids may be used, which may be those commercially available such as plasmid pBI101, they are preferably selected depending on their intended purpose. Particularly, when a large quantity of vector needs to be recovered, it is desirable to select a plasmid with a great number of copies. Further, the plasmid may be provided with a selection marker based on a drug such as neomycin or a nutrient (for example, amino acid requirement), the former of which serves as an indicator in introducing the expression vector into an organism or the like. By providing this selection marker, it is possible to select a plant into which the expression vector has been introduced as indicated by the selection marker.

The construction of the D-hordein expression suppressing vectors as described above requires manipulations related to gene cloning such as restriction enzyme treatment, DNA ligation, and transformation of *E. coli*., and these may be performed using the conventional techniques. For example, in these instances, Molecular Cloning (Sambrook, Fritsch, Maniatis, Cold Spring Harbor Laboratory) may be referred to.

4. Introduction to Plants of Expression Suppressing Nucleic Acid or Expression-Suppressing Vector Containing the Same The cells into which the expression suppressing nucleic acid or the expression-suppressing vector containing the same are preferably plant cells having regeneration capabilities. Such cells, for example, include immature embryo derived cells and anther-derived cells.

As to the introduction of nucleic acids, methods known in the art can be employed. Specifically, there are mentioned in addition to the polyethylene glycol method, electroporation, particle bombardment, the *Agrobacterium* technique, and the like.

5. Transformed Plants

The plant into which the expression suppressing nucleic acid or the expression-suppressing vector has been introduced as an exogenous DNA as described above is a transformed plant with traits different from those before transformation, which forms a new variety or line provided with such trait that D-hordein is not produced or its formation is reduced.

In addition, the transformed plant constructed according to the above-mentioned expression suppressing method can be crossed with other varieties or lines to produce plants having similar traits (e.g., reduced level of D-hordein). These essentially correspond to the transformed plants constructed by the expression suppressing method.

6. Assay and Qualitative Analysis of Gel Protein

The method for extracting and assaying gel protein from the seeds grown on a transformed barley can be performed according to a method known in the art. For example, the method of Smith and Lister (Smith and Lister (1983), Journal of Cereal Science 1:229–239) or the method of Skerritt and Janes (Skerritt and Janes (1992), Journal of Cereal Science 1:219–235) can be used. To examine the composition of the obtained gel protein, SDS polyacrylamide electrophoresis is effective, but high performance liquid chromatography can also be used. The identification of each of B-, C-, and D-hordeins can be done on the basis of the information known from their molecular weights. For example, Shewry (Shewry (1993), Barley: Chemistry and Technology. pp. 164: American Association of Cereal Chemists) may be referred to.

EXAMPLES

This invention will be described in detail by way of examples; however, it should not be limited to these examples.

Example 1

Construction of D-hordein Expression Suppressing Vectors

Figure 1:
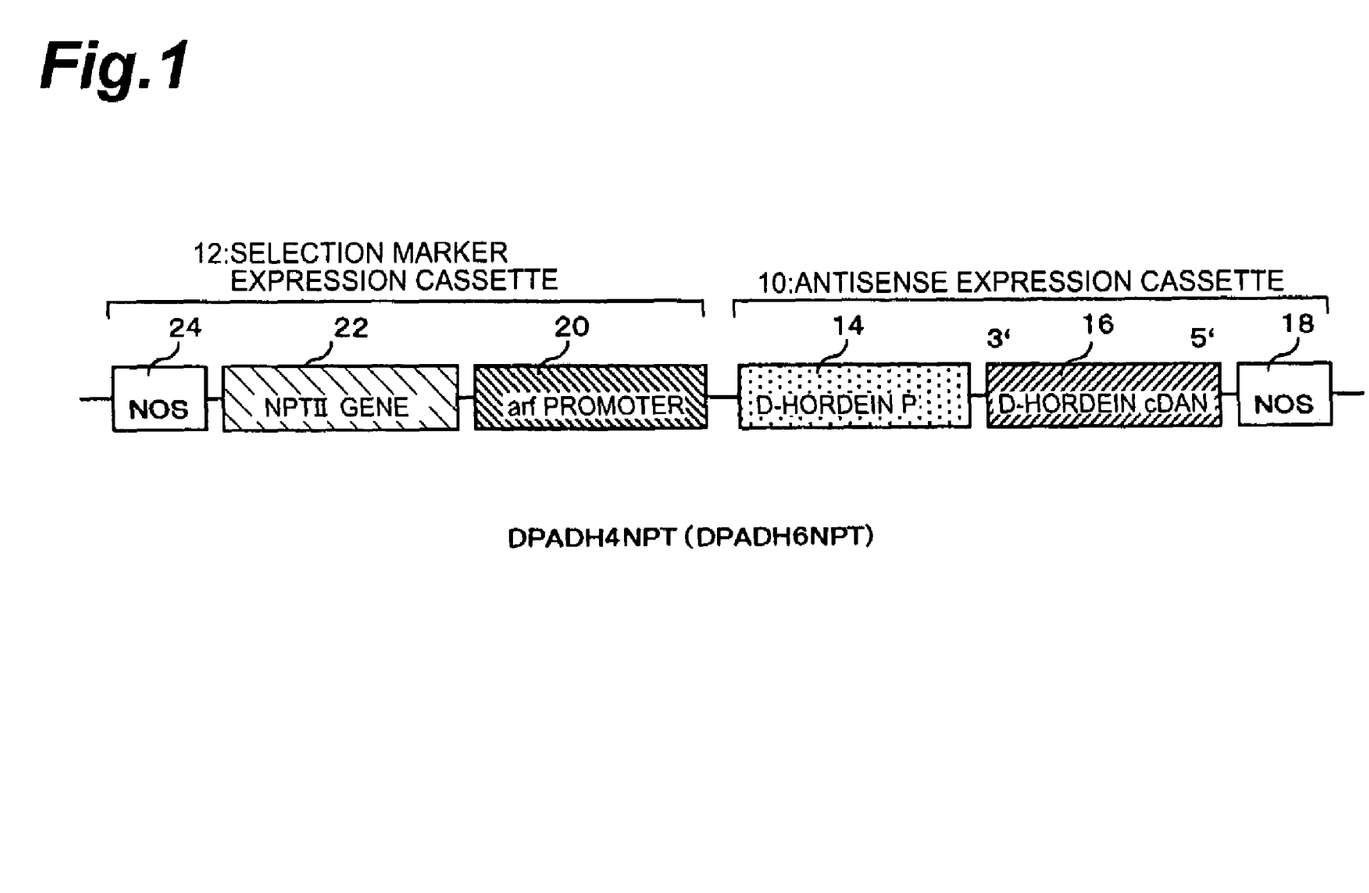
FIG. 1 is a graph showing the constitution of a D-hordein expression suppressing vector used in Example 1.

FIG. 1 shows the constitution of an expression-suppressing vector that expresses an antisense RNA to the D-hordein mRNA.

As shown in FIG. 1, the D-hordein expression suppressing vector is provided with antisense-expressing cassette 10 expressing the antisense RNA to the D-hordein mRNA, which serves as the D-hordein expression suppressing nucleic acid. In this antisense-expressing cassette 10, D-hordein cDNA 16 (SEQ NO:1 or 2) is linked to the downstream of D-hordein promoter (D-hordein P) 14 (SEQ NO:3) in a reverse orientation, i.e., 3'- to 5'-direction. NOS terminator 18 is further linked to the downstream of this inverted D-hordein cDNA 16.

The D-hordein expression suppressing vector is also provided with selection marker expressing cassette 12 in such a manner that its upstream faces the upstream of the above-mentioned antisense expressing cassette 10 (head to head); to this selection marker expressing cassette 12 is linked neomycin phosphotransferase (NPTII) gene 22 at the downstream of arf promoter 20 and is further linked NOS terminator 24.

Figure 2:
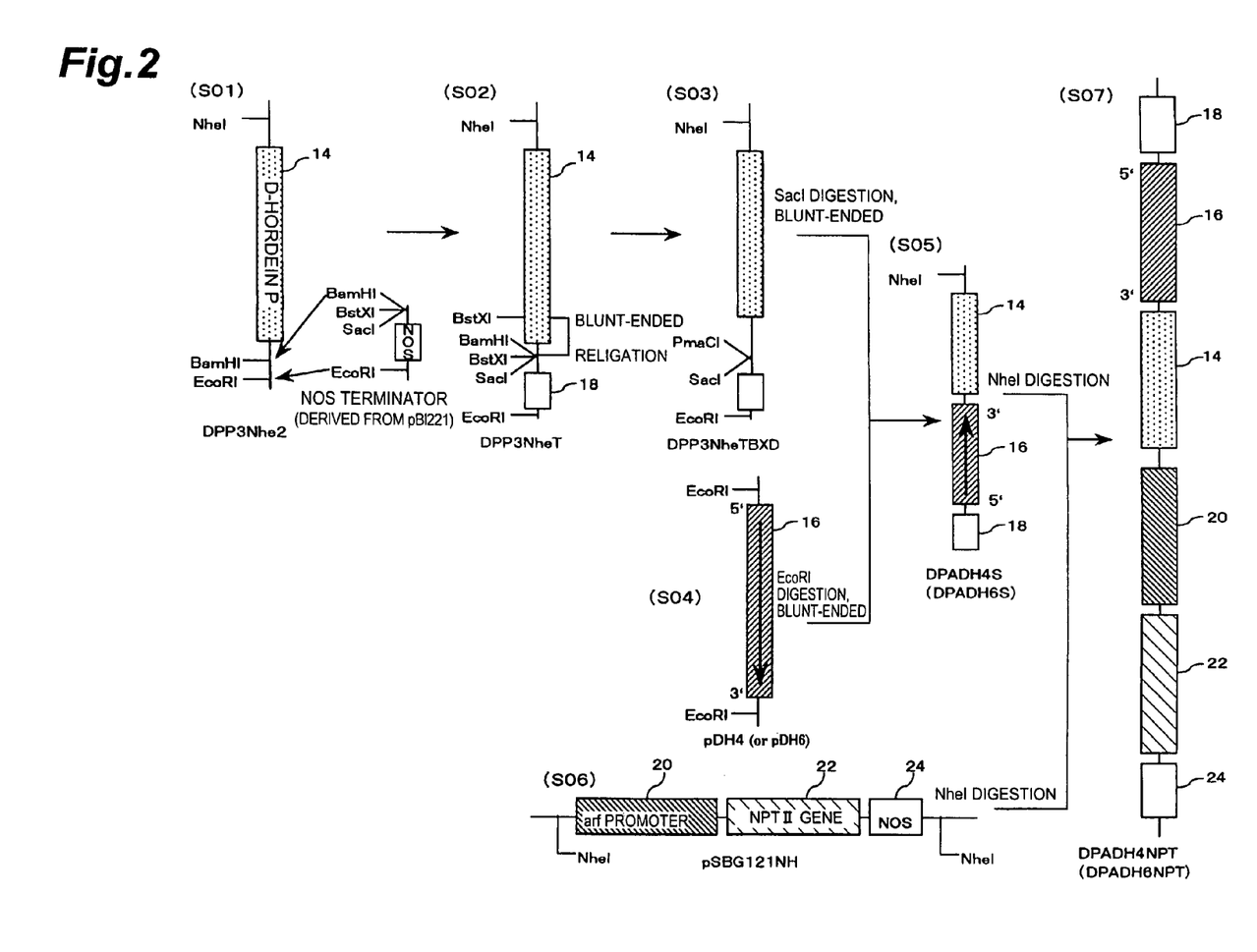
FIG. 2 is a graph showing a method for constructing the D-hordein expression suppressing vector used in Example 1.

FIG. 2 shows the construction of this D-hordein vector.

A vector supporting the DPP3 promoter (i.e., D-hordein promoter 14) was prepared, and the HindIII site (that is a multi-cloning site of this vector) was changed into a NheI site to produce a DPP3Nhe2 vector. This DPP3Nhe2 vector was digested with restriction enzymes, BamHI and EcoRI, and a BamHI-EcoRI fragment containing a NOS terminator 18 derived from pBI221 (BD Bioscience Clontech), which served as the transcription termination factor, was inserted therein and linked by ligation to produce DPP3NheT vector (SO2).

Subsequently, this DPP3NheT vector was digested with restriction enzyme BstX1 to make their ends blunt and after linkage again, DPP3NheTBXD vector (SO3) was obtained. The thus obtained DPP3NheTBXD vector has PmaCI and SacI sites between the D-hordein promoter and the NOS terminator.

The above-mentioned DPP3NheTBXD vector was then digested with SacI to prepare a segment with blunt ends (SO3). Separately, pDH4 or pDH6 supporting D-hordein cDNA16 was digested with EcoRI, whereby an EcoRI fragment containing the whole region of D-hordein cDNA (pDH4-derived: SEQ ID NO:1; pDH6-derived: SEQ ID NO:2) was prepared into a segment with blunt ends (SO4). These both segments were ligated and those in which the direction of D-hordein cDNA16 was in a reverse orientation to promoter 14 were selected and denoted DPADH4S and DPADH6S(SO5).

As noted above, in order to introduce selection marker expression cassette 12 into DPADH4S or DPADH6S vectors wherein antisense expression cassette 10 was formed, a selection marker expression cassette was prepared from pSBG121NH.

In this pSBG121NH, the neomycin phosphotransferase gene (Pharmacia; hereafter referred to as "nptII gene") is linked to the downstream of the arf promoter (SEQ ID NO:4) and the NOS terminator is further linked to the downstream thereof. Then, this pSBG121NH was digested with NheI to recover an expression cassette (SO6) containing NPTII gene 22. This segment was introduced into the NheI site of DPADH4S or DPADH6S described above. After its introduction, those in which selection marker expression cassette 12 and antisense expression cassette 10 were linked in a head-to-head manner were selected, and they were denoted DPADH4NPT and DPADH6NPT (SO7).

Example 2

Transformation of Barley

1. Transformation of Barley

The transformation of barley was carried out by introducing the D-hordein expression suppressing vector (DPADH4NPT or DPADH6NPT) into a protoplast obtained from a cell line derived from immature embryo of barley variety Igri according to the polyethylene glycol method.

Specifically, the two kinds of vector constructed in Example 1 were, respectively, purified using a Qiagen column (Qiagen Inc.), after which they were suspended in TE buffer (10 mM tris HCl (pH 7.5), 1 mM EDTA) to give a concentration of 1 µg/µl. Separately, the protoplast was prepared by subjecting the cultured cell line in liquid suspension of the Igri variety to enzymatic treatment and then to purification.

Vector introduction to this protoplast was essentially carried out according to the method of Funatsuki et al. (Funatsuki et al. (1995) Theoretical and Applied Genetics 91:707–712). Specifically, the resulting protoplast was suspended in 250 µl of Ca—S (calcium sorbitol solution) containing 50 µg of the above-mentioned vector, 100 mM CaCl$_2$, 0.6 M sorbitol, and 0.1(w/v)% of MES with the adjusted pH of 5.7.

To this suspension was dropwise added 600 µl of Ca—S PEG (pH 7.0) containing 40(w/v)% of PEG (polyethylene glycol, MW 1540), and after inverting several times, the suspension was allowed to stand for 5–10 minutes. After addition of LW solution (10 ml) and dilution, the protoplast was collected by centrifugation. This protoplast was suspended in 1 ml of a modified L1 medium (Lazzeri et al. 1991) containing 1.8% Sea Plaque Agarose (FMC Corporation) and 0.4 M maltose, and was cultured with nurse cells.

2. Selection of Vector-Introduced Colonies and Growth to Plant

Two to three weeks after the cultivation of the protoplast was initiated, the liquid medium and nurse cells were removed. Further, the resulting colonies were cultured in a liquid medium containing 20 µg/ml of or 25 µg/ml of G418 (geneticine available from Gibco-BRL) to select only the colonies containing the NPTII gene as the first selection.

After the G418 resistant colonies were shake-cultured for approximately 14 days, they were, for the second selection, transferred to and cultured in a regeneration medium which contained G418 at the same level as that used for the first selection. The colonies that showed the formation of callus and embryom or the differentiation of shoot during the second selection were transferred to a modified L3 medium which did not contain G418 so as to accelerate the regeneration of plantlet, which served as the transformed cell lines independently derived from the respective protoplasts. When the green shoot grew to be 1–2 cm, the culture dish was moved under the strong light. After cultivation, it was transferred to a culture medium with no hormone added; and shoot formation was accelerated and naturalization was carried out.

As a result of the above-mentioned transformation test, 18 lines (66 plants) were obtained from the group where the introduction of D-PADH4PT had been attempted; and 12 lines (29 plants) of regenerated plant were obtained from the group where the introduction of D-PADH6NPT had been attempted. The cultivation of all the provided barley plants was carried out in an artificially meteorological room which had been controlled at 16° C., 16 hours' day long, and 20000–30000 1× of lighting.

3. Identification of the Presence of Vector in Plant

Southern hybridization was used to confirm the presence or absence of the introduced D-hordein expression suppressing vector (DPADH4NPT or DPADH6NPT) in the regenerated plants.

First, 1 g of leaf of the regenerated plant was prepared and pulverized in liquid nitrogen, after which total DNA was extracted using the CTAB method (Murray et al. 1980, Nucleic Acids Res. 8: 4321–4325). The resulting DNA was subjected to agarose gel electrophoresis after digestion with HincII and it was capillary-blotted onto a nylon membrane (Boehringer Ingelheim) after alkaline denaturation. Vector pDH4R6 wherein the pDH4 insert had been ligated again in a reverse orientation was digested with HincII to produce an about 1.7 Kb fragment, which was labeled using DIG-high prime (Boehringer Ingelheim) and was used as a template to produce a probe for use.

The Southern hybridization was carried out according to the Manual of Boehringer. The washing of membrane after hybridization was as follows: after wash with 2×SSC and 1% SDS at room temperature for 30 minutes, wash with 0.1×SSC and 0.1% SDS at 42° C. for 30 minutes was repeated twice.

The signal detection method followed the Manual of Boehringer. Southern hybridization was carried out on each line of the obtained regenerated plants to detect transgene; as a result, the transgene was detected in 12 lines (48 plants) among the regenerated plants obtained from the group where the introduction of the D-hordein expression suppressing vector (DPADH4NPT) had been attempted as well as in 10 lines (23 plants) among the redifferentiated plants obtained from the group where the introduction of DPADH6NPT had been attempted.

Figure 3:
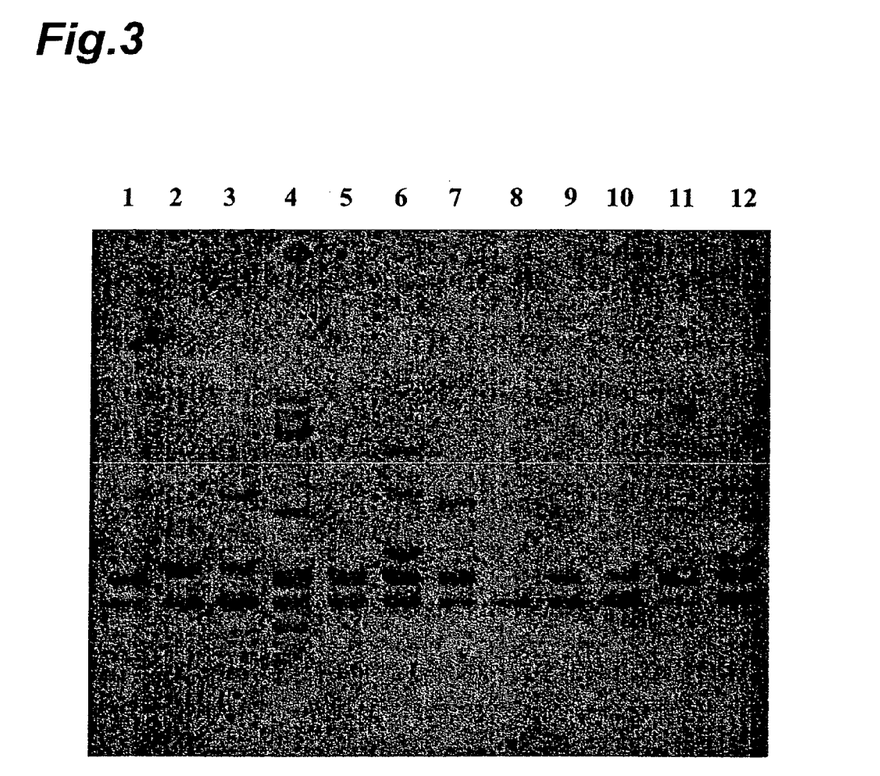
FIG. 3 is a graph showing the results from identification of the transgenes in transformed barleys in Example 2 by Southern blotting.

Note that when the transgene was detected in the representative of each line, all the plants belonging to the line were counted as presumably having the transgene. FIG. 3 shows the examples of transgene detection by Southern hybridization. This clearly confirmed that while only the signal of the endogenous D-hordein gene was detected in the DNA obtained from the regenerated plant used as the control into which no gene had been introduced (Lane 8 in FIG. 3), signals other than the endogenous gene, (i.e., transgenes) were present in the regenerated plants into which gene had been introduced (Lanes 1–7 and Lanes 9–12 in FIG. 3).

Example 3

Verification of the Effect of D-hordein Expression Suppressing Vector

The effect of the D-hordein expression suppressing vector was verified by determining the D-hordein content in the seed of the transformant through measurement of the band intensities of electrophoresis, which will be described below.

1. Extraction of Protein Fractions from Seed

Protein was extracted from the seed grown on the transformant for which the introduction of the D-hordein expression suppressing vector had been identified (which will be referred to as "T1 seed" hereafter) as described above. This extraction was as follows: one grain of the above-mentioned seed was finely pulverized with a hammer; USD buffer (8M urea, 0.1 M dithiothreitol, and 50.0 mM sodium carbonate) was added and agitated; and then incubation was conducted at 60° C. for 30minutes. This sample was then centrifuged at 15000 revolutions for 20 minutes to produce a transparent fraction (supernatant portion), which was collected.

2. Electrophoresis of Protein Fractions

Figure 4:
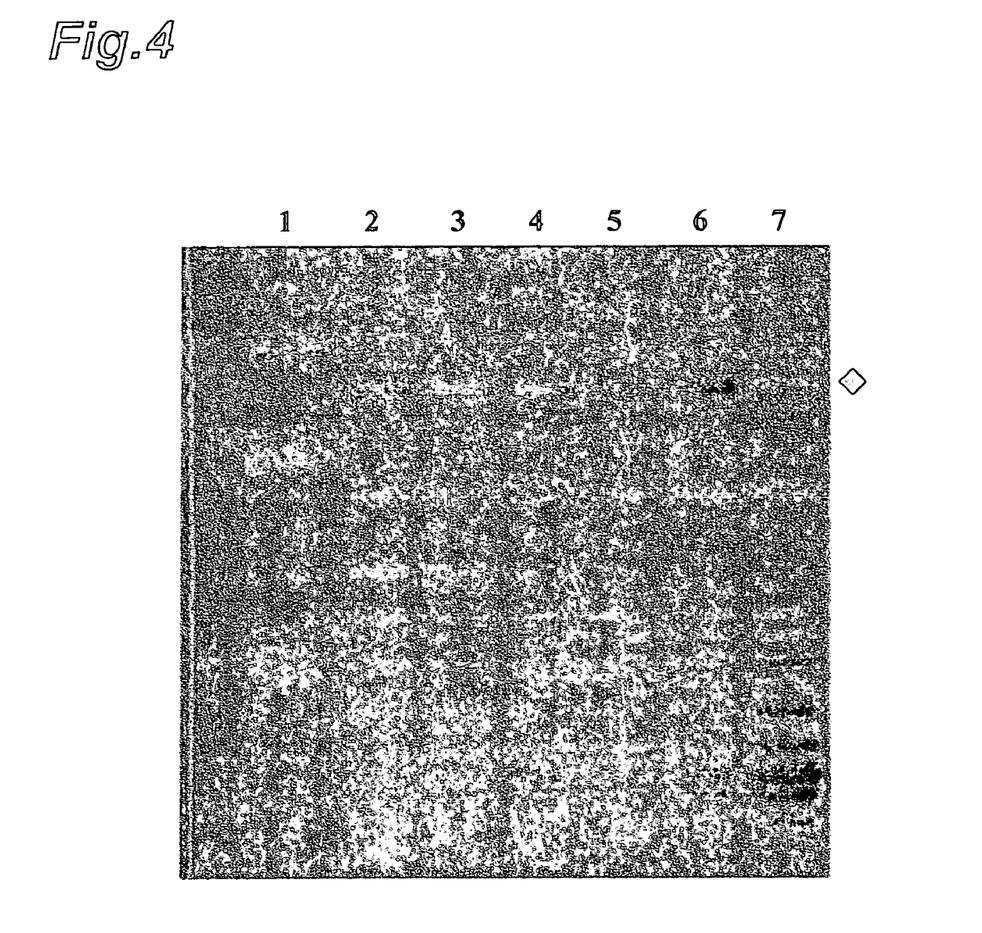
FIG. 4 is a graph showing the analysis by SDS polyacrylamide electrophoresis of hordein fractions from the seeds of transformed barleys in Example 3.

The supernatant fraction thus obtained was analyzed after fractionation using SDS polyacrylamide gel electrophoresis and staining with Coomassie Brilliant Blue R250. The results of analysis are shown in FIG. 4. In FIG. 4, the rhombus mark in black shows the band of D-hordein.

FIG. 4 shows, as an example, the electrophoresis of the USD buffer soluble fraction from the three grains of T1 seed belonging to the 90113AT15-1-4 line into which DPADH6NPT had been introduced. As the negative control, there were provided the commercially available Igri seed and the seed grown on the regenerated plant into which no gene had been introduced.

As FIG. 4 shows, it has become apparent that the content of D-hordein relative to the other hordeins has decreased drastically in Lanes 5 and 7 (which are the hordein fractions of the transformant) as compared to the non-transformed controls (Lanes 2, 3, and 4).

In addition, it has also become apparent that the relative content of D-hordein has decreased by comparison with the control in the other lines into which the D-hordein expression suppressing vector was introduced although there are some variations. It can thus be concluded that the D-hordein expression suppressing vector constructed according to this invention definitely has the effect of reducing D-hordein in the transformed barley specifically, i.e., with hardly altering the other hordein contents.

Further, no difference was observed between Lane 6 and the control, but this result can be explained by that it was caused due to the segregation of the transgene in the T1 seed. Therefore, this fact does not contradict the above-mentioned conclusion that the reduction of D-hordein results from the introduction of the D-hordein expression suppressing vector.

Example 4

Assay of Gel Protein

1. Recovery of gel protein from seed

The assay of gel protein was carried out by reference to Skerritt and Janes (Skerritt and Janes (1992), Journal of Cereal Science 16: 219–235).

The husk of one grain of the T1 seed obtained from the transformant was peeled off and finely pulverized with a hammer; it was put in a centrifugal tube the weight of which had been measured in advance. After drying with a Speed Vac Concentrator (Savant Instruments) for 30 minutes, the weight was measured to calculate the weight of the grain. To this sample was added 3 ml of 1.5(w/v)% SDS and it was agitated with a Vortex for 1 hour.

The sample after agitation was centrifuged at 40,000×g and 20° C. for 1 hour, and the resulting supernatant was denoted "SDS soluble fraction" (or "SDS fraction").

On the other hand, to the deposited fraction from the above-mentioned centrifugation was added 2 ml of 1.5(w/v)% SDS/10(v/v)% 2-mercaptoethanol/16(v/v)% N,N'-dimethylformamide (which will be referred to as "SDM" hereafter). After thorough agitation, incubation was carried out at 45° C. for approximately 20 hours. This sample after agitation was centrifuged at 40,000×g and 20° C. for 1 hour, and the resulting supernatant was subjected to dialysis using 0.2% SDS. This dialysis was carried out by repeating three rounds of 2 hours, and the volume was measured after the dialysis. The thus obtained fraction was "gel protein fraction" (or, "gel fraction").

2. Reduction of Gel Protein with Decreasing D-hordein

The protein assay of the above-mentioned SDS and gel fractions employed a BCA Protein Assay Reagent (Pierce Inc.), as well as bovine serum albumin as the standard protein. After the gel proteins of the transformants were assayed, the T1 seeds used were examined by the SDS polyacrylamide electrophoresis as described above for any reduction of D-hordein. This eliminated the data of the T1 seeds for which the segregation (dropout) of the transgene had caused the reduction of D-hordein to be unobservable.

Barley variety Igri and the regenerated barley lines having no transgene (90213AC1-5A, 90213AC1-6B, and 90213AC1-4B) were used as the negative controls; and the protein contents of the gel fractions obtained from the T1 seeds belonging to the trasnformant lines (90113AT-1-1-2C, 90113AT14-1-3C, 90113AT14-1-5G, and 90113AT15-1-4) into which the D-hordein expression suppressing vector had been introduced were examined.

Figure 5A:
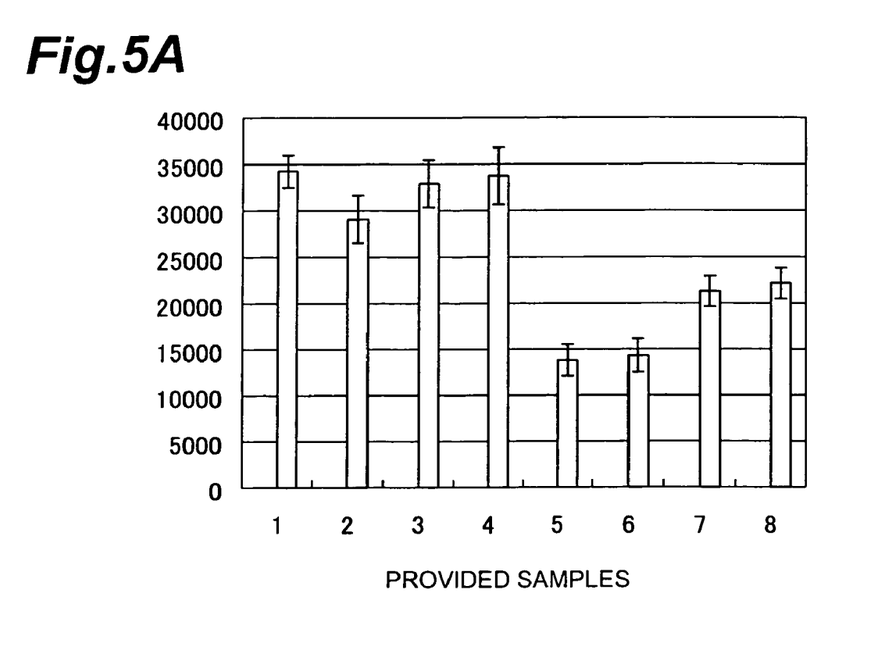
FIGS. 5A and 5B are graphs showing the results from the assay of gel protein in the seeds of transformed barleys in Example 4.

Extraction and assay were conducted on at least 5 samples for each line (n=≧5). FIG. 5A shows the gel protein content of the extracted gel fraction per gram of the sample as well as its standard deviation.

As the graphs in FIG. 5A clearly show, the group where the D-hordein content was reduced (FIG. 5A: 5, 6, 7, and 8) exhibited an obvious reduction in the gel protein content as compared to the negative controls (FIG. 5A: 1, 2, 3, and 4). It was also found that the average of the gel protein contents for all the samples of which D-hordein had been reduced was significantly lower (about 40% less on the average) than the average of all the samples from the negative controls: the level of significance was 1%. The foregoing results show that the reduction of the gel protein is not due to variations in culturing, but is an event resulting from the reduction of D-hordein.

3. Identification of Correlation Between the Reduction of D-hordein and the Reduction of Gel Protein In the T1 seeds grown on the same plant body, examination was made as to how the presence or absence of a reduction in the D-hordein content resulting from the segregation of the transgene changes the gel protein content.

Gel protein was extracted from 10 grains of the T1 seed obtained from the same plant body belonging to the 90113AT15-1-4 line and the quantities of reduction of D-hordein were qualitatively examined by electrophoresis. The 10 grains were classified into the group (5 grains) where the D-hordein quantity had been reduced and the group (5 grains) where the reduction had not been observed. These two groups were then used to examine the correlation between the presence or absence of reduction of D-hordein and the gel protein content. The results are shown in FIG. 5B.

Figure 5B:
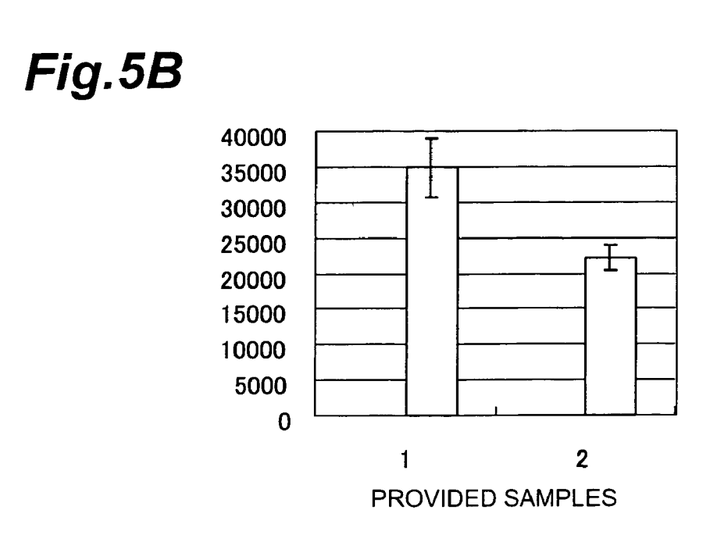

As FIG. 5B shows, it has become apparent that the gel protein content (FIG. 5B: Sample 2) for the seed group (5 grains) where the D-hordein content was reduced is significantly lower than the gel protein content (FIG. 5B: Sample 1) for the seed (5 grains) where no reduction of D-hordein content was observed: the level of significance was 1%.

Since this test was conducted on the seeds grown on the same plant body, the environmental differences that would be seen among individual plant bodies can be ignored. Accordingly, it has been shown that the reduction of the gel protein does not result from the environmental differences, but is the event resulting from the characteristics pertaining to the individual plants (i.e., specific reduction in the formation of D-hordein).

From the foregoing results, it can be concluded that a reduction in the gel protein content is made possible by the introduction of the D-hordein expression suppressing vector and the resultant reduction in the formation of D-hordein.

Example 5

Variation in the Composition of Gel Protein

The compositional variation of gel protein that the introduction of the D-hordein expression suppressing vector would induce was examined. The SDS fractions (Lanes 2, 3, 4, and 5 in FIG. 6) and gel fractions (Lanes 6, 7, 8, and 9 in FIG. 6), both of which were extracted from 90113AT15-1-4, were respectively analyzed by SDS polyacrylamide gel electrophoresis.

Figure 6:
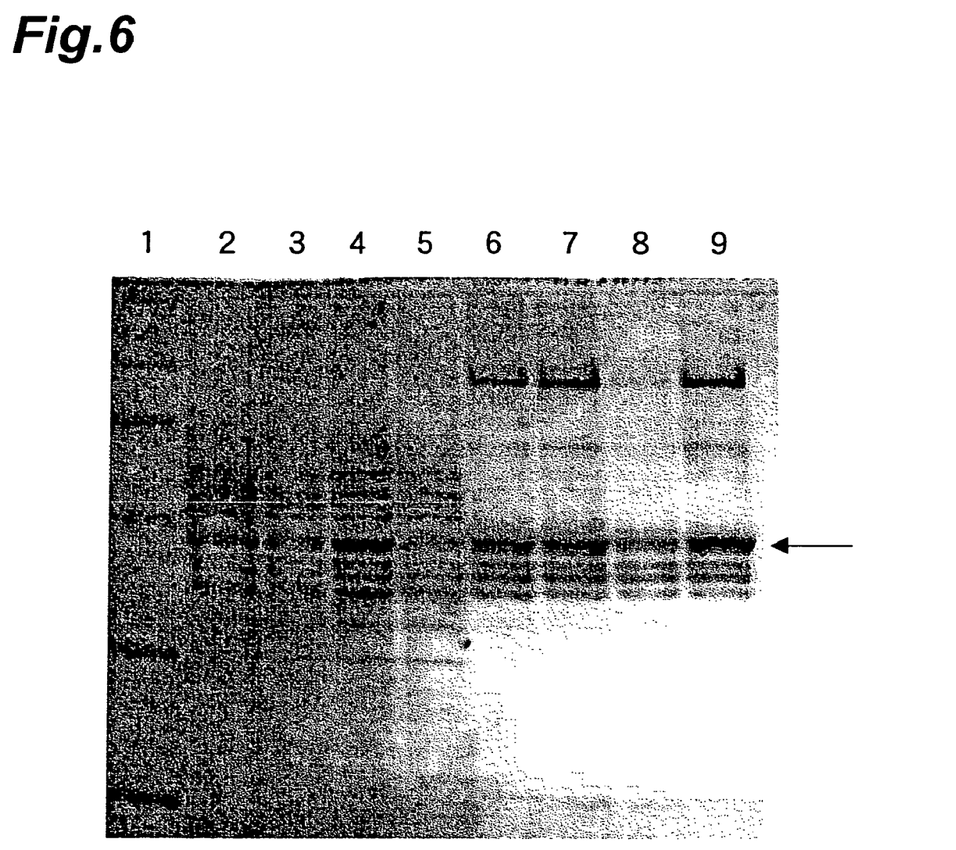
FIG. 6 is a graph showing variations in the composition of gel protein in the seeds of transformed barleys in Example 5.

Consequently, it has become apparent that in the T1 seeds having reduced D-hordein content (Lanes 4 and 8 in FIG. 6) as compared to the controls (Lanes 2, 3, 4, and 5 in FIG. 6) a specific protein that would naturally be extracted into the gel fractions (which will be hereafter referred to as "GS protein(s)" and which is indicated as an arrow in FIG. 6) has migrated to the SDS fractions.

This result suggests that the reduction of the gel protein resulting from the introduction of D-hordein expression suppressing vector is caused not only by a reduction of D-hordein, but also by concurrent elimination from the gel fraction of other proteins (which at least contain GS protein) constituting the gel protein.

Example 6

Transmission of the Introduced Trait to Progeny

Examination was made as to whether the introduced trait described above has been transmitted to the progeny. Gel protein was extracted from 7 grains of T2 seed having reduced D-hordein and was assayed; as a result, an average of 16.9 mg (+1.48) gel protein per gram of grain was extracted. This gel protein content was at almost the same level as the parent T1 seed having reduced D-hordein. It has become clear that the trait of the reduced gel protein is consistently transmitted to the progeny.

INDUSTRIAL APPLICABILITY

It has become clear that the barley with about 40% reduction of gel protein which presumably has a high correlation with wort filterability and wort extract quantity can readily and efficiently be constructed according to this invention. By utilizing this invention, it is possible to reduce time and labor that is required by conventional cross breeding and mutation breeding as well as to produce barleys with reduced gel protein without the use of breeding fields or X-ray irradiation devices which have been necessitated by those methodologies.

The invention claimed is:

1. A method for producing a barley with reduced gel protein content in which the gel protein is capable of agglutinating in a gel during the extraction of proteins from the barley, said method comprising:

introducing into the barley, a D-hordein expression suppressing nucleic acid which comprises a nucleic acid having the sequence of SEQ ID NO: 1 or 2, wherein said nucleic acid having the sequence of SEQ ID NO: 1 or 2 is linked in a reverse orientation downstream of a promoter operable within the barley and wherein said D-hordein expression suppressing nucleic acid generates an antisense RNA complementary to the endogenous D-hordein RNA of barley, whereby the production of D-hordein is suppressed and the gel protein content is thus reduced.

2. A D-hordein expression suppressing nucleic acid comprising a nucleic acid having the sequence of SEQ ID NO: 1 or 2, wherein said nucleic acid having the sequence of SEQ ID NO: 1 or 2 is linked in a reverse orientation downstream of a promoter operable within the barley and wherein said D-hordein expression suppressing nucleic acid generates an antisense RNA complementary to the endogenous D-hordein RNA of barley.

3. A vector comprising the D-hordein expression suppressing nucleic acid according to claim 2.

4. The vector according to claim 3, wherein a selection marker expression cassette capable of expressing a selectable marker is provided in the vicinity of the D-hordein expression suppressing nucleic acid.

5. A kit for producing a barley with reduced gel protein content comprising the D-hordein expression suppressing nucleic acid according to claim 2, wherein the D-hordein expression suppressing nucleic acid can be introduced into the barley and the gel protein content of the barley is thus reduced.

6. A barley produced by the method according to claim 1.

7. A kit for producing a barley with reduced gel protein content comprising the vector according to claim 3, wherein the vector can be introduced into the barley and the gel protein content of the barley is thus reduced.

8. A kit for producing a barley with reduced gel protein content comprising the vector according to claim 4, wherein the vector can be introduced into the barley and the gel protein content of the barley is thus reduced.

9. A barley comprising the D-hordein expression suppressing nucleic acid according to claim 2.

10. A barley comprising a D-hordein expression suppressing nucleic acid which comprises a nucleic acid having the sequence of SEQ ID NO: 1 or 2, wherein said nucleic acid having the sequence of SEQ ID NO: 1 or 2 is linked in a reverse orientation downstream of a promoter operable within the barley and wherein said D-hordein expression suppressing nucleic acid generates an antisense RNA complementary to the endogenous D-hordein RNA of barley, wherein the barley is produced by the kit of claim 5.

11. A barley comprising a D-hordein expression suppressing nucleic acid which comprises a nucleic acid having the sequence of SEQ ID NO: 1 or 2, wherein said nucleic acid having the sequence of SEQ ID NO: 1 or 2 is linked in a reverse orientation downstream of a promoter operable within the barley and wherein said D-hordein expression suppressing nucleic acid generates an antisense RNA complementary to the endogenous D-hordein RNA of barley, wherein the barley is produced by the kit of claim 7.

12. A barley comprising a D-hordein expression suppressing nucleic acid which comprises a nucleic acid having the sequence of SEQ ID NO: 1 or 2, wherein said nucleic acid having the sequence of SEQ ID NO: 1 or 2 is linked in a reverse orientation downstream of a promoter operable within the barley and wherein said D-hordein expression suppressing nucleic acid generates an antisense RNA complementary to the endogenous D-hordein RNA of barley, wherein the barley is produced by the kit of claim 8.

* * * * *